United States Patent [19]

Johnson et al.

[11] Patent Number: 4,927,902

[45] Date of Patent: May 22, 1990

[54] POLYTHIOLS AND USE AS EPOXY RESIN CURING AGENTS

[75] Inventors: Grannis S. Johnson, Maplewood; Reuben H. Grinstein, Denville; Stuart J. Hartman, Livingston; Raymond P. Dallago, Highland Park, all of N.J.

[73] Assignee: Henkel Corporation, Ambler, Pa.

[21] Appl. No.: 400,057

[22] Filed: Aug. 29, 1989

Related U.S. Application Data

[62] Division of Ser. No. 156,692, Feb. 17, 1988, Pat. No. 4,879,414.

[51] Int. Cl.$^5$ .............................................. C08G 59/66
[52] U.S. Cl. ..................................... 528/99; 528/109; 528/361; 528/374; 525/504
[58] Field of Search ................. 528/99, 109, 361, 374; 525/504

[56] References Cited

U.S. PATENT DOCUMENTS

| | | | |
|---|---|---|---|
| 2,951,822 | 9/1960 | Reinking | 528/119 X |
| 2,998,451 | 8/1961 | Boenig | 528/85 X |
| 3,258,495 | 6/1966 | Le Fave et al. | 528/374 X |
| 3,403,131 | 9/1968 | Garnish | 528/365 X |
| 3,595,882 | 7/1971 | Bremmer | 564/335 X |
| 3,598,748 | 8/1971 | Hirosawa | 528/63 X |
| 3,843,565 | 10/1974 | Yamamoto et al. | 528/298 X |
| 4,177,173 | 12/1979 | Carr | 528/88 |
| 4,383,090 | 5/1983 | Slocki et al. | 525/502 |
| 4,429,158 | 1/1984 | Good et al. | 564/455 |

FOREIGN PATENT DOCUMENTS 54-128531 10/1979 Japan.

OTHER PUBLICATIONS

Gaylord, "Polyethers", Interscience, New York, 1962, pp. 8–10.
Burness et al., J. Org. Chem., 28, 2283 (1963).

*Primary Examiner*—Earl Nielsen
*Attorney, Agent, or Firm*—Ernest G. Szoke; Wayne C. Jaeschke; Norvell E. Wisdom, Jr.

[57] ABSTRACT

Polythiols prepared by the reaction of hydrogen sulfide or organic dithiols with polyglycidyl substituted amines have been found to be outstanding curing agents for epoxy resins. Epoxy resins cured with these polythiols are characterized by not only improved gel times, but also improved cure rates, better heat resistance and greater resistance to absorption of water.

A useful polythiol is the reaction product of N,N,N',N'-tetraglycidyl-m-xylylenediamine with hydrogen sulfide.

23 Claims, No Drawings

POLYTHIOLS AND USE AS EPOXY RESIN CURING AGENTS

This is a division of Ser. No. 156,692, filed 2/17/88, now U.S. Pat. No. 4,879,414.

BACKGROUND OF THE INVENTION

1. Field of the Invention

This invention relates to new polythiols and their use in curing or hardening polyepoxide resins to produce hard, insoluble, infusible films, castings and adhesives.

2. Description of the Prior Art

Polyglycidyl ethers, particularly those prepared from a dihydric phenol such as Bisphenol A, i.e., 2,2- bis(4-hydroxyphenyl)propane, and an epihalohydrin such as epichlorohydrin, also referred to as epoxy resins, epoxide resins, polyepoxide resins or polyepoxides are important commercial products. When cured, these thermosetting resins form insoluble, infusible films, pottings, castings, adhesives, and the like, and are markedly superior in their physical, chemical, and electrical properties to many other cured thermosetting resins. They exhibit low shrinkage during curing. The combination of hardness and toughness exhibited by the cured resins, their high adhesive strength, resistance to degradation by solvents and other chemicals and their electrical properties, such as dielectric constant and resistivity, are outstanding. At the same time, these properties can be varied within wide limits depending on the end use intended for the resin. Of the wide variety of hardeners, curing agents, or homopolymerization catalysts which have been used to cure polyepoxide resins, no one is suitable for all applications, and many have serious drawbacks no matter what the application.

Among the curing agents for epoxy resins are polythiols, generally used in combination with tertiary amines as catalyst or accelerator. See, for example U.S. Pat. No. 3,258,459 —Le Fave et al, June 28, 1966 describing use of thiol terminated polyoxyalkylene glycols in combination with a tertiary amine accelerator and U.S. Pat. No. 4,177,173 —Carr, Dec. 4, 1979 describing a curing system for polyepoxide resins composed of polymercaptan and poly [(N,N-dimethylamino) alkyl] ethers as catalyst.

SUMMARY OF THE INVENTION

New polythiols prepared by the reaction of hydrogen sulfide or organic dithiols with polyglycidyl substituted amines have been found to be outstanding curing agents for epoxy resins. Epoxy resins cured with one or a mixture of these novel polythiols are characterized by not only faster gel times, but also by improved cure rates, better heat resistance and greater resistance to chemicals and water absorption. Further, since these polythiols contain tertiary nitrogen, it has been found that they can be utilized without need for additional tertiary amine catalyst.

DESCRIPTION OF THE PREFERRED EMBODIMENTS

Polythiol

The polythiols have the following structure:

(XSCH$_2$CHOHCH$_2$)$_b$-A-R-N(CH$_2$CHOHCH$_2$SX)$_2$ wherein

R is aromatic, substituted aromatic, methylene bis-diphenyl, xylylene, cycloaliphatic, substituted cycloaliphatic, methylene bis-dicyclohexyl, dimethylene cyclohexyl, methylene cyclohexyl or aliphatic, A is N (nitrogen) or O (oxygen), X is -H or -R'SH, R' is alkylene, cycloalkylene or alkylene substituted aromatic, and when b is 1 when A =O and b is 2 when A is N.

Examples of R are:

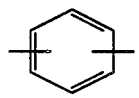

(phenylene) where the reactive positions are the 1, 2; 1,3 and 1,4 positions;

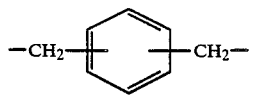

(xylylene) where the methylene groups are in the 1, 2; 1, 3 or 1, 4 positions;

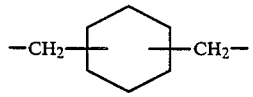

where the methylene groups are in the 1, 2; 1, 3 or 1, 4 positions (dimethylene cyclohexyl);

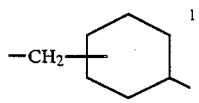

where the methylene group is in the 2, 3 or 4 position;

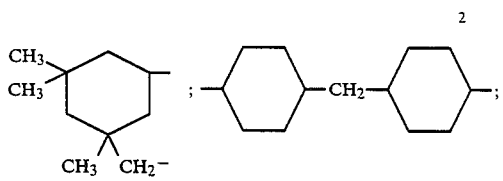

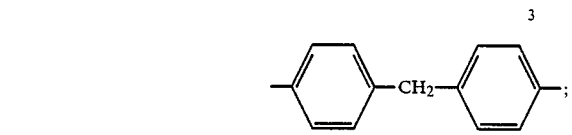

and (CH$_2$)$_n$ were n is from 2 to about 12.

Examples of R' are:

(CH$_2$CH$_2$)$_n$ where n is from 2 to about 12;

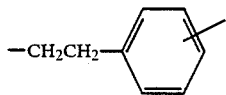

and

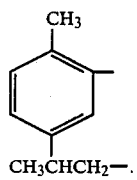

Examples of polythiols are:

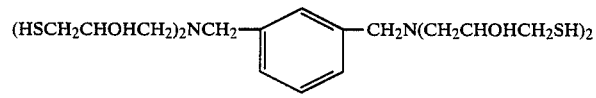

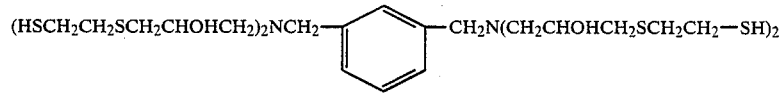

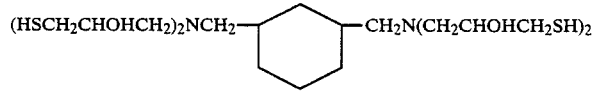

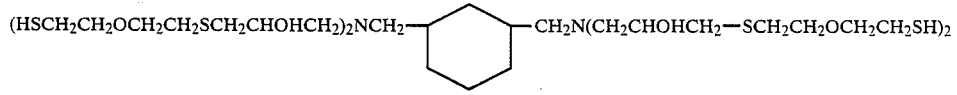

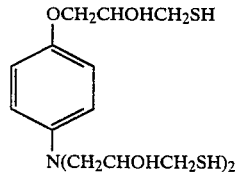

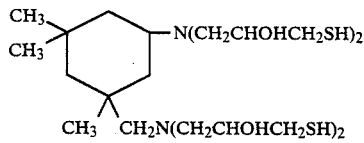

Burness et al, J. Org. Chem., 28, 2283 (1963) disclose monofunctional 3-diethylamino-2-hydroxypropyl mercaptan and difunctional 3-ethylamino bis-(2-hydroxypropyl mercaptan), neither of which is aromatic, cycloaliphatic or aliphatic. Monofunctional mercaptans have no utility as epoxy hardeners except perhaps, if their viscosities are very low, as viscosity reducers for high viscosity and/or solid multifunctional mercaptans. A difunctional mercaptan will react with standard difunctional epoxy resins, but primarily linear cross-linking is obtained. Thus, desirable properties resulting from high density cross-linking such as resistance to water absorption and heat cannot be obtained unless either or both the mercaptan or the epoxy resin is at least trifunctional.

The polythiols are prepared by reaction of hydrogen sulfide or organic dithiols with polyglycidyl amines. The preparation of polyglycidyl amines is well known in the art. See for example U.S. Pat. No. 3,843,565 —Kyoto et al, October 22, 1974 for the preparation of N,N,N'N'-tetraglycidyl bisaminomethyl cyclohexanes, Japanese 79-128531, Oct. 5, 1979 for the preparation of tetraglycidyl meta xylylenediamine and tetraglycidyl bisaminomethyl cyclohexane and U.S. Pat. No. 2,951,822 —Reinking, Sept. 6, 1960 for the preparation of polyglycidyl derivatives of aromatic amines. See also Burness et al, J. Org. Chem., 28, 2283 (1963).

In brief, amines of the structure:

$(H)_b$-A-R-NH$_2$ 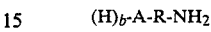

where R, A and b are defined above are reacted first with epihalohydrin such as epichlorohydrin or epibromohydrin and the resulting halohydrin then reacted with alkali to form polyglycidyl amine of the structure:

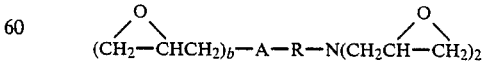

where R, A and b are defined above.

Thereafter, the polyglycidyl amine is reacted with hydrogen sulfide or organic dithiol such as 1,2-ethane dithiol and dimercapto diethyl ether to form polythiol. Reaction of 2,3-epoxypropyldiethylamine and 1N,N-bis (2,3-epoxypropyl) ethylamine with hydrogen sulfide has been described by Burness et al, J. Org. Chem., 28, 2283 (1963). Generally, this reaction is run by pumping polyglycidyl amine into a reactor containing solvent and catalyst and pressurized to a moderate level with hydrogen sulfide. Pressure is maintained throughout the reaction to provide a constant excess of hydrogen sulfide in order to minimize reaction of thiol groups in the forming polythiol with the incoming epoxide groups.

More specifically, polyglycidyl amines are prepared by adding amines slowly to excess epihalohydrin at moderate temperatures as a first step. The excess of epihalohydrin is necessary to ensure complete reaction of the amine group with the full complement of epihalohydrin. The excess of epihalohydrin is generally three to five moles per mole of primary amine group. The exact excess may vary depending on the particular amine being used. The temperature of addition of amine to epihalohydrin can be from about 25 deg. C to 50 deg. C. Lower temperatures result in a slow reaction time while higher temperatures promote detrimental side reactions.

This is followed by dehydrohalogenation of the resulting halohydrin by addition of strong base at moderate temperatures. Dehydrohalogenation can also best be achieved at temperatures of 25 deg. C to 50 deg. C. Again, very low temperatures result in sluggish reactions while high temperatures promote the formation of by-products. The excess epihalohydrin may be left in the mixture during dehydrohalogenation and then removed later by vacuum distillation. Alternatively, in some cases, it may be possible to remove the excess epihalohydrin by vacuum distillation prior to dehydrohalogenation.

Bases that are effective in dehydrohalogenation include the alkali and alkaline earth metal hydroxides, sodium hydroxide, potassium hydroxide, calcium hydroxide and magnesium hydroxide being the most common. Tetra alkyl ammonium hydroxides would be equally effective. In general, it is necessary to employ an excess of the strong base to achieve complete dehydrohalogenation and thus epoxide formation. This excess will be from 15 to 50% molar excess for each mole of epoxide to be formed.

Isolation of the polyglycidyl amines is achieved by adding water to dissolve the salt which is a by-product of the dehydrohalogenation step followed by phase separation. The amount of water added is calculated to result in complete dissolution of the salt with high salt concentrations. The product layer containing unreacted epihalohydrin will be the upper layer. This layer is isolated and vacuum stripped to remove excess epihalohydrin. The material left behind is the polyglycidylamine.

The polyglycidyl amine is then reacted with hydrogen sulfide or dithiol to form polythiol. The polyglycidyl amine is first pumped into a reactor pressurized with hydrogen sulfide and containing solvent and catalyst. Thus, there is present an excess of hydrogen sulfide over stoichiometric needs. After all the polyglycidylamine has been added, stirring under a pressure of hydrogen sulfide is continued until there is no further pressure drop. This indicates that no further reaction is taking place. The excess hydrogen sulfide is released to a caustic scrubber. The product is then isolated by stripping off the solvent under reduced pressure. Where practical, the inorganic sulfides resulting from reaction of the catalyst with hydrogen sulfide may be filtered off, either before or after stripping off the solvent.

Catalysts which are most effective are the alkali metal hydroxides or alkoxides such as sodium hydroxide, potassium hydroxide, sodium methoxide or tetraalkyl ammonium hydroxides such as tetramethyl ammonium hydroxide generally at a level of about 0.1% to about 5.0% based on the weight of polyglycidyl amine. Typically, sodium hydroxide in the form of an aqueous solution is used at a level of about 0.5% to about 2% based on the weight of the polyglycidyl amine.

Solvents which can be used depend on the solubilities of both the polyglycidyl amines as well as the polythiol products. For effective conversion of polyglycidyl amines to polythiols, a solvent which dissolves both the reactants and the product and is inert to the reactants should be employed. Solvents include the monomethyl, ethyl and butyl ethers of ethylene glycol, the monomethyl ether of propylene glycol, dimethyl formamide, isopropyl alcohol, methyl alcohol and the dimethyl ether of diethylene glycol. Optionally, water may be present as a cosolvent for the catalyst.

Hydrogen sulfide pressures may be relatively low, in the order of about 20 to about 60 psi although higher pressures would not be detrimental, but then also would not offer any great advantage in these reactions.

The temperature required for reaction of hydrogen sulfide with polyglycidyl amines is low, typically about 25 deg. C to about 50 deg. C. The rate at which the polyglycidyl amine is pumped into the reactor can vary. Good results have been obtained where the rate has been as slow as 0.3% of the total weight of polyglycidyl amine per minute to over 1% per minute.

When reacting a dithiol with a polyglycidyl amine, no solvent is required. Polyglycidyl amine is pumped into a reactor containing a stoichiometric excess of dithiol and catalyst at a rate of about 0.1 to about 5.0% of the total weight to be added per minute at about 25 deg. C to about 100 deg. C. After completion of the addition of the polyglycidylamine to the dithiol, stirring is continued at the same temperature until analysis shows the absence of oxirane oxygen. Isolation of the product is achieved by distilling unreacted dithiol at reduced pressure leaving behind the product.

There should be at least two moles of dithiol for each mole of oxirane oxygen in the polyglycidyl amine during the reaction. Larger excesses of dithiol can be used without detrimental effect.

Polyepoxide

Concerning the nature of the polyepoxides, these are well-known materials and the curing of same described herein is not limited to any particular polyepoxide. It is only necessary that there be more than one vicinal 1,2-epoxide group per molecule in the polyepoxide. The polyepoxide may be saturated or unsaturated, aliphatic, cycloaliphatic, aromatic or heterocyclic and may be substituted with substituents, such as chlorine, hydroxy groups, ether groups and the like. It may be monomeric or polymeric. Many polyepoxides, particularly those of the polymeric type, are described in terms of their epoxy equivalent. An explanation of same appears in U.S. Pat. No. 2,633,458 —Shokal, Mar. 31, 1953 (see 25 column 3, lines 3-34). The polyepoxides used herein are those having an epoxy functionality greater than 1.0, that is to say, that the number of epoxy groups per molecule, according to the expression, functionality is equal to molecular weight divided by epoxide equivalent, is greater than one.

To obtain a rapid cure rate at room temperature or below, it is preferred that the epoxide group be activated by an adjacent electron withdrawing group as in the glycidyl ethers, glycidyl esters, glycidyl thio ethers and glycidyl amines. Exemplary, although not limiting, are one or more of the following epoxides.

Polyepoxides that may be used in this invention are disclosed in U.S. Pat. No. 2,633,458 —Shokal, Mar. 31, 1953. Those portions of this patent which disclose examples of polyepoxides are incorporated by reference herein.

Other examples include the epoxidized esters of polyethylenically unsaturated monocarboxylic acids, such as epoxidized linseed, soybean, perilla, oiticica, tung, walnut, dehydrated castor oil, methyl linoleate, butyl linoleate, ethyl 9,12-octadecadienoate, butyl 9,12,15-octadecatrienoate, butyl eleostearate, monoglycerides of tung oil fatty acids, monoglycerides of soybean oil, sunflower, rapeseed, hempseed, sardine, cottonseed oil and the like.

Another group comprises the epoxidized polyethylenically unsaturated hydrocarbons, such as epoxidized 2,2-bis (2-cyclohexenyl) propane, epoxidized vinyl cyclohexene and epoxidized dimer of cyclopentadiene.

Another group comprises the epoxidized polymers and copolymers of diolefins, such as butadiene. Examples include butadiene-acrylonitrile copolymers (Hycar rubbers, B.F. Goodrich) butadiene-styrene copolymers, etc.

Another group comprises the glycidyl containing nitrogen compounds such as diglycidyl aniline, the tetraepoxide of methylene dianiline and the triepoxide of amino phenol.

Polyepoxides particularly useful in the compositions of this invention are the glycidyl ethers of polyhydric phenols, including bis-phenols and novolacs and polyhydric alcohols. The glycidyl ethers of polyhydric phenols are obtained by reacting epichlorohydrin with the desired phenols in the presence of alkali. Polyether A and Polyether B described in U.S. Pat. No. 2,633,458 are examples of polyepoxides of this type. Other examples include the diglycidyl ether of 2,2-bis (4-hydroxyphenyl) propane, the diglycidyl ether of bis (4-hydroxyphenyl) methane, the polyglycidyl ether of 1,1,2,2-tetrakis (4-hydroxyphenyl) ethane (epoxy value of 0.45 eq./100 g. and melting point 85 deg. C), the polyglycidyl ether of 1,1,5,5-tetrakis (hydroxyphenyl) pentane (epoxy value of 0.514 eq./100 gram) and their mixtures.

Novolac resins are produced by reaction of formaldehyde with a phenol, for example, phenol, alkyl, aryl or polyhydroxy phenols. The resulting polyglycidyl ethers are then prepared by reaction of an epihalohydrin, usually epichlorohydrin, with the novolac. Useful molecular weight range for the novolacs is from about 300 to about 1,000.

Further, useful polyepoxides are glycidyl ethers from polyhydric alcohols such as glycerine, pentaerythritol, 1,2,6-hexanetriol and trimethylolpropane; glycidyl esters such as diepoxides prepared from phthalic acid, tetrahydrophthalic acid, hexahydrophthalic acid and dimer acids.

Catalysts, preferably one or more tertiary amine catalysts, are used with the polythiols in the curing or hardening of the polyepoxide. Examples are aromatic ring-containing aliphatic tertiary amines such as 2,4,6-tri-(dimethylaminomethyl) phenol, benzyl dimethyl amine, dimethylaminomethyl phenol and poly [(N,N-dimethylamino) alkyl] ethers such as 2-(N,N-dimethylamino) ethyl 3-(N,N-dimethylamino) n-propyl ether.

Viscosity Reducers

At room temperature, some of the polythiol products are of high viscosity or are solid. This does not facilitate easy handling or mixing. Consequently, for applications as an epoxy hardener it is desirable to lower viscosity to a more handleable level. This can be accomplished in various ways with the use of nonreactive diluents, reactive diluents and other low viscosity epoxy hardeners. Examples are dibutyl phthalate, benzyl alcohol, limonene dimercaptan, polyethylene glycols, triphenylphosphite and gamma-butyrolactone.

Ancillary Ingredients

Curable polyepoxide compositions containing the novel polythiols of the present invention can also contain conventional fillers, extenders, solvents and the like. For example, when using curable polyepoxide compositions as protective coatings, commonly used organic solvents can be present, e.g., aromatic hydrocarbons such as benzene, toluene and xylene, ketones such as methyl ethyl ketone and methyl iso-butyl ketone, ethers such as dioxane, tetrahydrofuran, tetrahydropyran, ethylene glycol monoethyl ether acetate, diethylene glycol monoethyl ether acetate, dipropylene glycol monoethyl ether acetate, higher polyethylene and polypropylene glycol ethers and ether esters, and the like, as well as mixtures thereof. Similarly, fillers such as sand, silica, flour, aluminum silicate, clays, asbestos, Wollastonite, barytes, marble chips, marble dust, glass fibers, carbon black, titanium dioxide and the like, can be employed when the curable polyepoxide compositions are used for such purposes as sealants or adhesives, or in terrazzo tile or in castings or the like. Compositions may also contain catalyst promoters such as hydroxyl compounds as in alcohols. Also employed are flexibilizers such as epoxidized glycols, high molecular weight dimercapto polysulfide polymers such as Thiokol LP-3 and epoxy terminated copolymers such as Kelpoxy G272-100 (Spencer Kellogg) and plasticizers such as dibutyl phthalate. The filler volume concentration can vary from about 0% to about 80% of the total system. It should be noted that care must be exercised when using ancillary materials of an acidic nature where cure retardation is not desirable.

To improve odor, a reodorant or deodorant may also be included in the formulation. Generally, from about 0.1 to about 0.5% by weight reodorant is used based upon the weight of the hardener.

Optionally, additional polythiol (polymercaptan) can be present in varying amounts depending upon the desired curing characteristics of the epoxy system and depending upon the desired properties of the fully cured system.

Useful additional polythiols or polymercaptans are those prepared from polyepoxides having an epoxy functionality greater than one, i.e., the number of epoxy groups contained in the average polyepoxide molecule is greater than one. Such polyepoxides are converted to polymercaptans by reaction with hydrogen sulfide or by first converting the epoxide groups to halohydrin groups and thereafter reacting the halohydrin groups with a sulfhydrate such as sodium sulfhydrate or potassium sulfhydrate.

Polyepoxides which can be used in forming the polymercaptans include the reaction product of a halogen-containing epoxide such as epihalohydrin with an aliphatic polyhydric alcohol, e.g., glycerol, pentaerythritol, 1,2,6-hexanetriol, or 1,3,5-pentanetriol. Since secondary alcohols are formed, it is then necessary to reform the epoxide ring by further reaction with caustic. Suitable epoxides for reaction with hydrogen sulfide can also be formed by reaction between aromatic polyhydric phenols such as resorcinol, catechol or bisphenol and halogen-containing epoxide such as epihalohydrin or 3-chloro-1,2-epoxybutane and by reacting a polyhydric phenol or aliphatic polyhydric alcohol with a polyepoxide compound such as bis (2,3-epoxypropyl) ether, bis (2,3-epoxy-2-methylpropyl) ether. Since secondary alcohols are formed in the first instance, it is then necessary to reform the epoxide ring by further reaction with caustic.

Preferred are limonene dimercaptan and those prepared by initially reacting a polyhydric alcohol such as 1,2,6-hexanetriol, glycerol, trimethylol propane or pentaerythritol with an alkylene oxide, such as propylene oxide or ethylene oxide, there usually being a substantial molar excess of alkylene oxide present during reaction. Thereafter the resulting polyoxyalkylene-modified polyhydric alcohol is reacted with a halogen containing epoxide, e.g., an epihalohydrin or 3-chloro 1,2-epoxybutane, to prepare a halogenated polyhydric polyether from which the corresponding mercaptan polymer is obtained by reaction with a metallic sulfhydrate such as sodium sulfhydrate. Such resins include those disclosed in U.S. Pat. No. 3,258,495 - LeFave et al, June 28, 1966. Those portions of this patent which disclose examples of polymercaptans are incorporated by reference herein. These polymercaptans usually have an average molecular weight range of from about 250 to about 7,000 and -SH functionality between about 2.0 and about 6.

Other useful polymercaptans are tris(mercaptoalkyl) cyclohexanes such as 1,2,4-tris (2-mercaptoethyl) cyclohexane and 1,3,5-tris (2-mercaptoethyl) cyclohexane.

Another group is polymercaptoalkyl esters of polycarboxylic acids containing at least eighteen carbon atoms prepared by reacting mercapto alcohols containing up to ten carbon atoms with the appropriate polycarboxylic acid such as those commonly referred to as polymeric fatty acids.

Curing

When curing epoxy resins, the resin, one or more polythiol, preferably with tertiary amine catalyst and, optionally, diluents, fillers and the like, are brought together and blended by simple mixing. Curing occurs spontaneously with the evolution of heat.

The proportions of resin, polythiol, catalyst and diluent are as follows.

There is used from about 0.1 to about 1.5 equivalents of at least one polythiol per epoxide equivalent. Catalysts are not required to initiate crosslinking with the products of this invention, but are preferred. If used, they can be present in amounts of from about 0.1 to about 20.0 per cent by weight based on the weight of the polythiol.

Diluents and other such modifiers are optional and are primarily used to adjust viscosity and/or introduce flexibility to the cured resin/hardener. Theoretically, there is no limit to the amount of diluent that can be added. However, practical experience indicates that this should be a maximum of 35 per cent by weight of the curing system.

For a fuller understanding of the nature and advantages of this invention, reference may be made to the following examples. These examples are given merely to illustrate the invention and are not to be construed in a limiting sense. All quantities, proportions and percentages are by weight and all references to temperature are deg. C. In the following examples, the various properties were measured as described below.

Heat Distortion Temperature (HDT)

The Society of The Plastics Industry, Epoxy Resin Formulators Test Method ERF 17-82, similar to ASTM D-648.

Hardness, Persoz

ASTM D-4366-84, Hardness of Organic Coatings by Pendulum Damping Tests, Method B (Persoz Hardness Test).

Gel Time

Epoxy resin and the hardener being evaluated are blended in correct proportion and thoroughly mixed. The mixture is poured onto a flat surface to a depth of 0.30 inches and gel time measured. Gel time is taken as the time elapsed between the onset of mixing and that point at which the hardener/epoxy resin no longer adheres to a wooden probe.

Water and Chemical Resistance

Epoxy resin and the hardener being evaluated are blended in correct proportion and thoroughly mixed. The mixture is cast into ¼ inch thick, 2 inch diameter discs (approximately 20 grams).

The discs are weighed and immersed in distilled water or designated chemical at 22–25 deg. C. After predetermined time, the discs are removed from the water or chemical, towel dried and reweighed. Per cent weight increase, i.e., water or chemical absorption is calculated.

EXAMPLE I

Reaction of $H_2S$ with N,N,N'N'tetraglycidyl-m-xylylenediamine

Dimethyl formamide (300 grams) was charged into a 2 liter stainless steel reactor. The reactor was pressurized to 50 psi with hydrogen sulfide. An exotherm was observed. The reactor contents were cooled to 30 deg. C.

A solution of 321 grams N,N,N',N' tetraglycidyl-m-xylylenediamine and 100 grams of dimethyl formamide was prepared. This solution was pumped into the reactor at 2.5 ml per minute at 29–33 deg. C while maintaining hydrogen sulfide pressure at 40–50 psi. When addition was complete, a line rinse of 100 grams dimethyl formamide was pumped in. The reactor contents were stirred at about 33 deg. C with hydrogen sulfide feed shut off until no further drop in pressure was discernible. Excess hydrogen sulfide was released to a caustic scrubber. Solvent was removed by distilling under vacuum at up to 115 deg. C and at 36 mm. Hg. pressure.

Analysis of the resulting product showed a thiol content of 5.6 meq./gram. The product was highly viscous and barely mobile at room temperature. It had a viscosity of 32,000 cps at 70 deg. C.

EXAMPLE II

Reaction of hydrogen sulfide with
N,N,N',N'tetraglycidyl-1,3-bis-(aminomethyl)
cyclohexane Butyl Cellosolve (ethylene glycol monobutyl ether) (320 grams) and water (80 grams) were charged into a two liter stainless steel reactor. The reactor was pressurized to 50 psi with hydrogen sulfide. A solution of 300 grams N,N,N',N'tetra-glycidyl-1,3 bis-(aminomethyl) cyclohexane, 80 grams butyl Cellosolve and 20 grams of water was prepared. This solution was pumped into the reactor at 1.25–2.5 ml. per minute. Pressure of hydrogen sulfide in the reactor was maintained at 40–50 psi during this addition. Temperature was maintained at 29–36 deg. C. After completion of this addition, 110 ml of butyl Cellosolve was pumped in as a line rinse. The reactor contents were stirred until there was no further drop in pressure. Excess hydrogen sulfide was vented to a caustic scrubber. The reactor contents were transferred to a distillation flask. Solvent and water were removed by vacuum distillation, finally reaching 126 deg. C at 14 mm. Hg. pressure at the completion of the strip.

Analysis of the product which was highly viscous showed a thiol content of 6.61 meq./gram. yield was 380 grams (92.5% of theory). The product was highly viscous and barely mobile at room temperature.

EXAMPLE III

Reaction of a dithiol with a tetraglycidyldiamine 1,2-Ethanedithiol (251 grams, 2.67 moles) was charged into a one liter glass reactor. Triisopropylamine (2.0 gram) was added as catalyst. Then, 120 grams (0.33 mole) of N,N,N',N' tetraglycidyl-m-xylylenediamine were added dropwise. The mixture was heated gradually to 90 deg. C and maintained at 90-100 deg. C until thiol analysis showed that no further reaction was taking place. Excess ethanedithiol was then distilled off at reduced pressure, finishing off at a temperature of 120 deg. C and a pressure of 40 psi. Yield of product was 244 grams.

Analysis of product showed a thiol content of 5.45 meq./gram. The product was extremely viscous and barely mobile at room temperature.

EXAMPLE IV

Reaction of N,N,N',N'
Tetraglycidyl-m-xylylenediamine with hydrogen
sulfide - with sodium hydroxide catalyst Methyl Cellosolve (ethylene glycol monomethyl ether) (474 grams) and a 30% by weight aqueous solution of sodium hydroxide (8.0 ml.) were charged into a stainless steel pressure reactor. The reactor was charged with hydrogen sulfide to a pressure of 50 psi. There was an exothermic reaction with the temperature of the reactor contents rising from 24 deg. C to 32 deg. C.

A solution containing 1070 grams N,N,N',N' tetraglycidyl-m-xylylenediamine and 210 grams methyl Cellosolve was prepared. This solution was pumped into the reactor at the rate of 3.0 ml. per minute while maintaining a pressure of hydrogen sulfide in the reactor at about 50 psi. The temperature was maintained at 32-39 deg. C. After the solution was added, a line rinse of 100 ml. of methyl Cellosolve was pumped in. The reactor contents were stirred with the hydrogen sulfide intake turned off until there was no further pressure drop. The hydrogen sulfide was then vented to a caustic scrubber. The reactor contents were transferred to a distillation flask where solvent was removed by distillation at reduced pressure, eventually reaching a temperature of 119 deg. C at 50 mm. Hg. pressure.

Yield of product was 1373 grams with a thiol content of 6.31 meq./gram. and the product was highly viscous and barely mobile at room temperature.

EXAMPLE V

Reaction of N,N,N',N'
Tetraglycidyl-1,3-bis-(aminomethyl) cyclohexane with
hydrogen sulfide use of sodium hydroxide catalyst,
methyl Cellosolve solvent Methyl Cellosolve (320 grams) and water (80 grams) were charged into a stainless steel reactor. 30% by weight aqueous solution of sodium hydroxide (6.0 ml) was added as catalyst. Hydrogen sulfide gas was charged into the reactor to a pressure of 50 psi. N,N,N',N'tetraglycidyl-1,3-bis-(aminomethyl) cyclohexane (700 grams) was pumped in slowly. Pressure of hydrogen sulfide was maintained at 40-50 psi. The temperature was maintained at 26-38 deg. C by external cooling. After completion of this addition, 100 ml of methyl Cellosolve was pumped in as a line rinse. The reaction was then stirred until no further pressure drop was evident. Hydrogen sulfide was vented to a caustic scrubber. Solvent and water were removed by distillation at reduced pressure, up to 110 deg. C at 40-60 mm. Hg.

Analysis of the resulting end product showed a thiol content of 7.10 meq./gram. and the product was a highly viscous, barely mobile material at room temperature.

EXAMPLE VI

Reaction of
N,N,N',N'tetraglycidyl-1,3-bis-(aminomethyl)
cyclohexane with hydrogen sulfide use of diethylene
glycol dimethyl ether as solvent Into a two liter stainless steel reactor were charged 200 ml. diethylene glycol dimethyl ether, 165 ml. of water and 5 ml. of a 50% by weight aqueous solution of sodium hydroxide. The mixture was stirred and hydrogen sulfide charged into the reactor to a pressure of 40 psi. A solution of 500 grams N,N,N'N'tetraglycidyl-1,3-bis (aminomethyl) cyclohexane and 300 grams of diethylene glycol dimethyl ether was prepared. This solution was pumped into the reactor at the rate of 6.0 ml./minute while maintaining hydrogen sulfide pressure at 40 psi with the temperature at 30-35 deg. C. After completion of the addition, the hydrogen sulfide feed was shut off and the reaction was continued until there was no further pressure drop. The hydrogen sulfide was vented to a caustic scrubber. The reactor contents were transferred to a distillation flask where the solvent and water were recovered by distillation at reduced pressure. Final temperature was 108 deg. C with the pressure at 7 mm. Hg.

Analysis of the resulting product showed a thiol content of 7.47 meq./gram and a viscosity of 32,000 cps at 70 deg. C. At room temperature the product was a soft solid.

EXAMPLE VII

Reaction of N,N,N',N'tetraglycidyl-m-xylylenediamine with hydrogen sulfide -use of 1-methoxy-2-propanol as solvent The procedure of Example VI was followed. Initial charge into the reactor was 220 grams of 1-methoxy-2-propanol (Arcosolve PM), 5 ml. of a 50% by weight aqueous solution of sodium hydroxide and 30 ml water. Hydrogen sulfide pressure of 40 psi was maintained while a solution of 500 grams of N,N,N',N'-tetraglycidyl-m-xylylenediamine in 500 ml of Arcosolve PM was pumped in at 6 ml./min. Temperature was maintained at 30-35 deg. C.

Solvent recovery was accomplished by distillation at 30 mm. Hg and up to 108 deg. C.

The resulting product had a thiol value of 6.81 meq./gram. and was highly viscous and barely mobile.

EXAMPLE VIII

Reaction of N,N,N',N'tetraglycidyl-1,3-bis-(aminomethyl) cyclohexane with hydrogen sulfide -use of 1-methoxy 2-propanol as solvent The procedure of Example VI was followed. Initial charge in the reactor was 200 grams 1-methoxy-2-propanol (Arcosolve PM), 5.0 ml. of a 50% by weight aqueous solution of sodium hydroxide and 50.0 ml. water. A solution of 530 grams N,N,N',N'tetraglycidyl-1,3-bis-(aminomethyl) cyclohexane in 530 grams Arcosolve PM was pumped in at the rate of 6 ml./min. while hydrogen sulfide pressure was maintained at 40 psi. Temperature was maintained at 30-35 deg. C. Solvent recovery was accomplished by vacuum distillation up to 110 deg. C at 20 mm. Hg.

Analysis of the product showed a thiol content of 6.68 meq./gram. The product was highly viscous and barely mobile at ambient temperature.

EXAMPLE IX

Reaction of 1-[N,N-(2,3 epoxy propyl)-amino]-4-(2,3 epoxy propoxy)-benzene with hydrogen sulfide Into a two liter stainless steel reactor were charged 200 ml. 1-methoxy-2-propanol (Arcosolve !M) and 5.0 ml. 50% sodium hydroxide. The reactor was evacuated and then pressurized to 40 psi with hydrogen sulfide. A solution of 456 grams of 1-[N,N-(2,3 epoxy propyl)-amino]-4-(2,3-epoxy propoxy)-benzene in 400 ml. of Arcosolve PM was pumped into the reactor in 2.5 hours while maintaining the pressure of hydrogen sulfide at 40 psi and the temperature at 30 deg. C. After reacting out, solvent was recovered by vacuum distillation at 50 mm. Hg and up to 110 deg. C.

Analysis of the resulting trithiol indicated a thiol content of 6.98 meq./gram which was in agreement with the calculated value. The product was a highly viscous almost solid material at room temperature.

The polyglycidyl amine had the following structure:

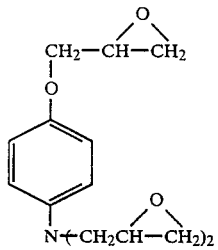

EXAMPLE X

A. Preparation of N,N,N',N'tetraglycidyl 3-aminomethyl-3,5,5-trimethyl cyclohexylamine Epichlorohydrin (650 grams) was charged into a 2 liter reaction flask equipped with stirrer, condenser, thermometer and dropping funnel. Water (265 grams) was added. This mixture was then heated to 35 deg. C. 3-Aminomethyl-3,5,5-trimethyl cyclohexylamine, also referred to as isophorone diamine, (120 grams) was added dropwise to the flask contents at 35-40 deg. C in about one-half hour. The resulting mixture was stirred at 35-40 deg. C. for two and one-half additional hours. Analysis at this point indicated complete reaction of the amine group with epichlorohydrin. 50% by weight aqueous solution of sodium hydroxide (260 grams) was added dropwise in forty minutes at 35-40 deg. C. Stirring was continued at this temperature range for an additional three hours. Water (400 grams) was added to dissolve the salt formed as a by-product. The entire reaction mixture was transferred to a separatory funnel and let stand until the upper product layer containing unreacted epichlorohydrin and the lower aqueous layer had separated completely. The aqueous layer was drained off and discarded. To the organic (product) phase were added 26 grams of 50% by weight solution of sodium hydroxide. The resulting mixture was steam distilled at reduced pressure to remove unreacted epichlorohydrin and then finally dried by vacuum stripping. The resulting product was then cooled down and filtered. There was obtained 201 grams of a viscous clear colorless liquid with a Brookfield viscosity at 25 deg. C of 24,000 cps.

Analysis showed a combined amine and oxirane oxygen content of 14.8 meq./gram (calc. 15.2 meq./gram).

B. Reaction of tetraglycidyl diamine of Part A with hydrogen sulfide

Into a stainless steel reactor were charged 200 grams of 1-methoxy-2-propanol and 2.5 grams of 50% by weight solution of sodium hydroxide. The reactor was evacuated and recharged with hydrogen sulfide gas to a pressure of 40 psi. The product of Part A (100 grams), dissolved in 100 grams of 1-methoxy-2-propanol, was pumped into the reactor at 6 ml./min. while maintaining a pressure of hydrogen sulfide of 40 psi and a temperature of 30 deg. C. The reaction was then brought to completion by maintaining a temperature of 30 deg. C at 40 psi of hydrogen sulfide for one and one-half hours. Unreacted hydrogen sulfide was released to a caustic scrubber. The mixture was distilled up to a temperature of 120 deg. C and a pressure of 50 mm. of Hg. A liquid product remained which solidified at room temperature. This was then ground to give a white powder which on reheating melted at 70–75 deg. C. The thiol content was 6.35 meq./gram.

EXAMPLE XI

Evaluation of the Polythiol of Example I

The product of Example I was mixed with equal parts by weight of a curing system composed of a simple blend of (a) 44.8 parts by weight of the polymercaptan described below, (b) 44.8 parts by weight of limonene dimercaptan, (c) 2.5 parts by weight of 2-(N,N-dimethylamino) ethyl 3-(N,N-dimethylamino) n-propyl ether and (d) 7.4 parts by weight of 2,4,6 tri (dimethylaminomethyl) phenol to form the hardener.

The polymercaptan component (a) above is based on a propylene oxide derivative of pentaerythritol of molecular weight of about 400–410 which is reacted with epichlorohydrin. The resulting epichlorohydrin adduct is dehydrochlorinated with sodium hydroxide to form the polyepoxide which is converted with hydrogen sulfide to polymercaptan of molecular weight of about 870, a viscosity at 25 deg. C of 15,000 cps. (Brookfield viscosity) and a mercaptan equivalent weight of 280. It is characterized by a hydroxyl group beta to each mercaptan group.

The mixture of the product of Example I and the curing system prepared above was combined by hand at room temperature with an epoxy resin in a weight ratio of 75 parts by weight mixture to 100 parts by weight of epoxy resin. The epoxy resin had the following structure:

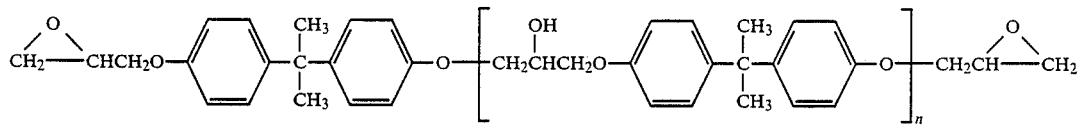

where n is approximately 0.09 and having an epoxide equivalent weight of 178–186 and a viscosity at 25 deg. C of 6,500–9,500 cps.

Gel time, heat distortion temperature and water absorption were determined. The water absorption and heat distortion temperature test specimens were allowed to cure for seven days at room temperature (22 deg. C –25 deg. C) before testing.

The processes and tests were repeated using the curing system described above in this example as the sole hardener. The following table gives results of these tests comparing this curing system with the 50/50 mixture of the curing system and the product of Example I.

TABLE I

|  | 50/50 Mixture of Product of Example I and Curing System | Curing System Alone |
|---|---|---|
| Gel Time | 5 min. 35 sec. | 6 min. |
| % Water Absorption (Immersion Temperature, 22-25 deg. C.) | | |
| 1 day | 0.11 | 0.47 |
| 7 days | 0.35 | 1.34 |
| 21 days | 0.67 | 2.35 |
| Heat Distortion Temperature, (deg. C.) | 64 | 54 |

In this and in other tables, the higher the per cent, the greater is the water absorption which is undesirable. In the case of heat distortion, the lower the temperature the greater the distortion which is undesirable.

EXAMPLE XII

Evaluation of the Polythiol of Example II

The produce of Example XI was followed using the polythiol of Example II in place of the polythiol of Example I. Results are tabulated below.

TABLE II

|  | 50/50 Mixture of Product of Example II and Curing System | Curing System Alone |
|---|---|---|
| Gel Time | 8 min. 2 sec. | 6 min. |
| % Water Absorption (Immersion Temperature, 22-25 deg. C.) | | |
| 1 day | 0.09 | 0.47 |
| 7 days | 0.32 | 1.34 |
| 21 days | 0.62 | 2.35 |
| Heat Duration Temperature, (deg. C.) | 68 | 54 |

EXAMPLE XIII

Evaluation of the POlythiol of Example III

The procedure of Example XI was again followed except for using the polythiol of Example III in place of the polythiol of Example I. Results are tabulated below.

TABLE III

|  | 50/50 Mixture of Product of Example III and Curing System | Curing System Alone |
|---|---|---|
| Gel Time | 5 min. 15 sec. | 6 min. |
| % Water Absorption (Immersion Temperature, 22-25 deg. C.) | | |
| 1 day | 0.12 | 0.47 |
| 7 days | 0.36 | 1.34 |
| 21 days | 0.66 | 2.35 |
| Heat Distorsion Temperature, (deg. C.) | 63 | 54 |

EXAMPLE XIV

Evaluation of Example VI

Since the polythiol of Example VI has a viscosity of 32,000 cps at 70 deg. C., benzyl alcohol, a viscosity reducer, was used. The following formulation was prepared by simple blending with good mechanical stirring until a homogeneous mixture was obtained.

| Components | % by Wt. |
|---|---|
| Polythiol of Example VI | 73.8 |
| Benzyl alcohol | 14.7 |
| 2,4,6-tri-(dimethylamino methyl) phenol (tertiary amine) | 7.4 |
| Limonene dimercaptan | 4.1 |
| | 100.0 |

The above formulation was blended with an epoxy resin, viz., the diglycidyl ether of Bisphenol A (epoxy equivalent weight of 180-195, visc. 11,000-15,000 cps). Heat distortion temperature, water absorption, chemical resistance and Persoz hardness were determined. See Tables IV, V and VI for the data. For comparison, data is included on several commercial products. These products include other mercaptans, polyamines and polyamides.

Although polyamines and polyamides represent different chemical classes of curing agents from mercaptans, they were included in the comparison because they are widely used in the epoxy industry. They are known for their excellent resistance to water absorption and the polyamines also for chemical resistance. Neither class is known to give the low temperature cure, thin film cure and extreme reactivity attributed to mercaptans. The comparison is intended to demonstrate that the products of this invention, in addition to exhibiting to a greater degree those advantages attributed to mercaptans, are also approaching the water and chemical resistances of polyamines and polyamides.

EXAMPLE XV

Evaluation of Example I

Since the polythiol of Example I has a viscosity of 32,000 cps at 70 deg. C., benzyl alcohol, a viscosity reducer, was used. The following formulation was prepared by simple blending with good mechanical stirring until a homogeneous mixture was obtained.

| Components | % by Wt. |
| --- | --- |
| Polythiol of Example I | 73.8 |
| Benzyl alcohol | 14.7 |
| 2,4,6-tri-(dimethylamino methyl) phenol | 7.4 |
| Limonene dimercaptan | 4.1 |
| | 100.0 |

The above formulation was blended with an epoxy resin, viz., the diglycidyl ether of Bisphenol A (epoxy equivalent weight of 180-195, visc. 11,000-15,000 cps). Heat distortion temperature, water, absorption, chemical resistance and Persoz hardness were determined. See Tables IV, V and VI for the data.

TABLE IV

Heat Distortion Temperature and Water Absorption[1]

| | | | Water Absorption % Wt. After Immersion for[3] | |
| --- | --- | --- | --- | --- |
| Hardener | PHR[2] | HDT (Deg. C.) | 24 Hrs | 7 Days |
| (a) Example XIV (containing polythiol of Ex. VI) | 65 | 58 | 0.18 | 0.47 |
| (b) Example XV (containing polythiol of Ex. I) | 65 | 56 | 0.14 | 0.49 |
| (c) Polymercaptan[4] based on propoxylated pentaerythritol | 100[5] | 56 | 0.40 | 2.20 |
| (d) Polyether amine[6] polymercaptan curing system | 80 | 54 | 0.30 | 1.30 |
| (e) Triethylene-tetra amine (TETA) | 14 | 60 | 0.14 | 0.32 |
| (f) Versamid 140[7] (polyamide) | 35 | 40 | 0.12 | 0.26 |
| (g) Versamine F-20[8] | 42 | 61 | 0.12 | 0.26 |

TABLE IV-continued

Heat Distortion Temperature and Water Absorption[1]

| | | | Water Absorption % Wt. After Immersion for[3] | |
| --- | --- | --- | --- | --- |
| Hardener | PHR[2] | HDT (Deg. C.) | 24 Hrs | 7 Days |
| (amine phenol-formaldehyde adduct) | | | | |

[1]Cure schedule 7 days at room temperature (22 deg. C.-25 deg. C.).
[2]PHR = Parts by weight hardener for every 100 parts by weight epoxy resin.
[3]Immersion temperature, 22-25 deg. C.
[4]See description in Example XI.
[5]Catalyzed with 2,4,6 tri(dimethylaminomethyl)phenol, 10% by weight based on the mercaptan hardener.
[6]Curing system of (a) polymercaptan based on propoxylated pentaerythritol, (b) limonene dimercaptan, (c) 2-(N,N-dimethylamino) ethyl 3-(N,N-dimethylamino) n-propyl ether and (d) 2,4,6 tri(dimethylaminomethyl) phenol described in Example XI.
[7]Available from Henkel Corporation, standard reactive polyamide resin based on dimerized fatty acid and polyamines.
[8]Available from Henkel Corporation.

TABLE V

Chemical Absorption

| | % Absorption After 7 Day Immersion at 22-25 Deg. C. | | | |
| --- | --- | --- | --- | --- |
| Chemical | Hardener[1] of Example XIV | Polmer-captan[1][4] | TETA[1][3] | TETA[2][3] |
| 10% NaOH | 0.23 | 0.30 | 0.38 | 0.36 |
| 10% HCl | 0.89 | 1.70 | — | 0.64 |
| 10% HNO$_3$ | 1.30 | 1.80 | — | 0.81 |
| 10% H$_2$SO$_4$ | 1.89 | — | — | — |

In the above table, all chemicals are percent by weight of chemical in water and all hardener concentrations are the same as in Table IV.
[1]Cured for 7 days at 22-25 deg. C. before immersion.
[2]Cured for 24 hours at 22-25 deg. C. plus 2 hours at 121 deg. C.
[3]Taken from Literature.
[4]Polymercaptan based on propoxylated pentaerythritol descibed in Example XI.

Measurements of hardness development by Persoz were conducted. These were performed on 4 ml coatings on cold rolled steel panels. Testing was done at room temperature. The higher the Persoz number, the harder the material tested. The data is reported in Table VI below. Hardener concentrations are the same as reported in Table IV.

TABLE VI

| | | Persoz Hardness | |
| --- | --- | --- | --- |
| Time, Minutes[a] | Polymercaptan[b] | Hardener of Example XIV | Hardener of Example XV |
| 7 | 0 | 130 | 130 |
| 10 | 0 | 191 | 180 |
| 17 | 0 | 239 | 220 |
| 30 | 0 | 275 | 260 |
| 40 | 23 | 283 | 280 |
| 50 | 29 | 299 | 288 |
| 60 | 35 | 309 | 295 |
| 120 | 65 | 308 | 298 |

[a]As measured from mixing of resin and hardener.
[b]Polymercaptan based on propoxylated pentaerythritol. See description in Example XI.

While the invention has been described with reference to certain specific embodiments thereof, it is understood that it is not to be so limited since alterations and changes may be made therein which are within the full and intended scope of the appended claims.

What is claimed is:
1. A curable epoxy resin comprising:
(a) at least one polyepoxide and

(b) at least one polythiol having the structure:

(XSCH$_2$CHOHCH$_2$)$_b$-A-R-N(CH$_2$COHOHCH$_2$SX)$_2$ wherein:
R is aromatic, substituted aromatic, methylene bis-diphenyl, xylylene, cycloaliphatic, substituted cycloaliphatic, methylene bisdicyclohexyl, dimethylene cyclohexyl, methylene cyclohexyl or aliphatic,
A is N or 0
X is -H or -R'SH,
R' is alkylene, cycloalkylene or alkylene substituted aromatic, and
when A is 0, b is 1 and when A is N, b is 2.

2. A curable epoxy resin comprising:
(a) at least one polyepoxide and
(b) at least one polythiol selected from the group consisting of:

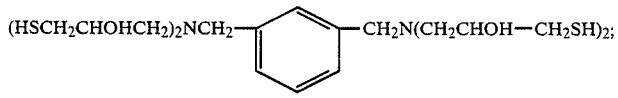
(HSCH$_2$CHOHCH$_2$)$_2$NCH$_2$—⟨phenyl⟩—CH$_2$N(CH$_2$CHOH—CH$_2$SH)$_2$;

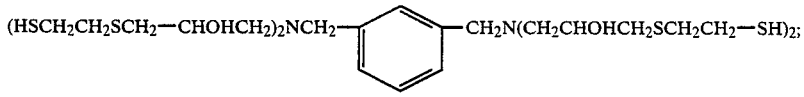
(HSCH$_2$CH$_2$SCH$_2$—CHOHCH$_2$)$_2$NCH$_2$—⟨phenyl⟩—CH$_2$N(CH$_2$CHOHCH$_2$SCH$_2$CH$_2$—SH)$_2$;

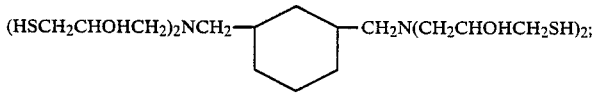
(HSCH$_2$CHOHCH$_2$)$_2$NCH$_2$—⟨cyclohexyl⟩—CH$_2$N(CH$_2$CHOHCH$_2$SH)$_2$;

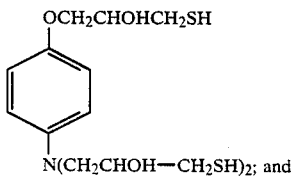
OCH$_2$CHOHCH$_2$SH
⟨phenyl⟩
N(CH$_2$CHOH—CH$_2$SH)$_2$; and

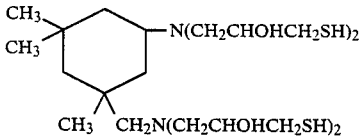
CH$_3$, CH$_3$ —⟨cyclohexyl⟩— N(CH$_2$CHOHCH$_2$SH)$_2$
CH$_3$  CH$_2$N(CH$_2$CHOHCH$_2$SH)$_2$ 3. The curable epoxy resin of claim 2 wherein said polythiol is:

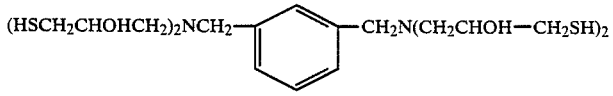
(HSCH$_2$CHOHCH$_2$)$_2$NCH$_2$—⟨phenyl⟩—CH$_2$N(CH$_2$CHOH—CH$_2$SH)$_2$ 4. The curable epoxy resin of claim 2 wherein said polythiol is:

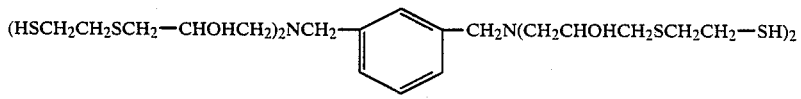
(HSCH$_2$CH$_2$SCH$_2$—CHOHCH$_2$)$_2$NCH$_2$—⟨phenyl⟩—CH$_2$N(CH$_2$CHOHCH$_2$SCH$_2$CH$_2$—SH)$_2$ 5. The curable epoxy resin of claim 2 wherein said polythiol is:

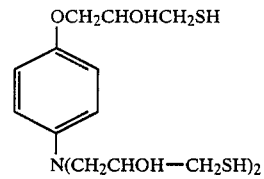
(HSCH$_2$CHOHCH$_2$)$_2$NCH$_2$—⟨cyclohexyl⟩—CH$_2$N(CH$_2$CHOHCH$_2$SH)$_2$ 6. The curable epoxy resin of claim 2 wherein said polythiol is:

OCH$_2$CHOHCH$_2$SH
⟨phenyl⟩
N(CH$_2$CHOH—CH$_2$SH)$_2$

7. The curable epoxy resin of claim 2 wherein said polythiol is:

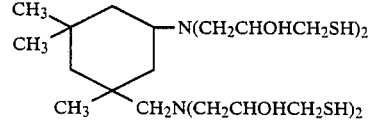
CH$_3$, CH$_3$ —⟨cyclohexyl⟩— N(CH$_2$CHOHCH$_2$SH)$_2$
CH$_3$  CH$_2$N(CH$_2$CHOHCH$_2$SH)$_2$

8. The curable epoxy resin of claim 1 wherein there is present tertiary amine catalyst.

9. A substantially insoluble and infusible product which is the reaction product of a polyepoxide composition comprising:
(a) at least one polyepoxide and
(b) at least one polythiol having the structure:

(XSCH₂CHOHCH₂)ᵦ-A-R-N
(CH₂COHOHCH₂SX)₂ wherein:
R is aromatic, substituted aromatic, methylene bisdiphenyl, xylylene, cycloaliphatic, substituted cycloaliphatic, methylene bisdicyclohexyl, dimethylene cyclohexyl, methylene cyclohexyl or aliphatic,
A is N or 0
X is -H or -R'SH,
R' is alkylene, cycloalkylene or alkylene substituted aromatic, and
when A is 0, b is 1 and when A is N, b is 2.

10. A substantially insoluble and infusible product which is the reaction product of a polyepoxide composition comprising:
(a) at least one polyepoxide and
(b) at least one polythiol selected from the group consisting of:

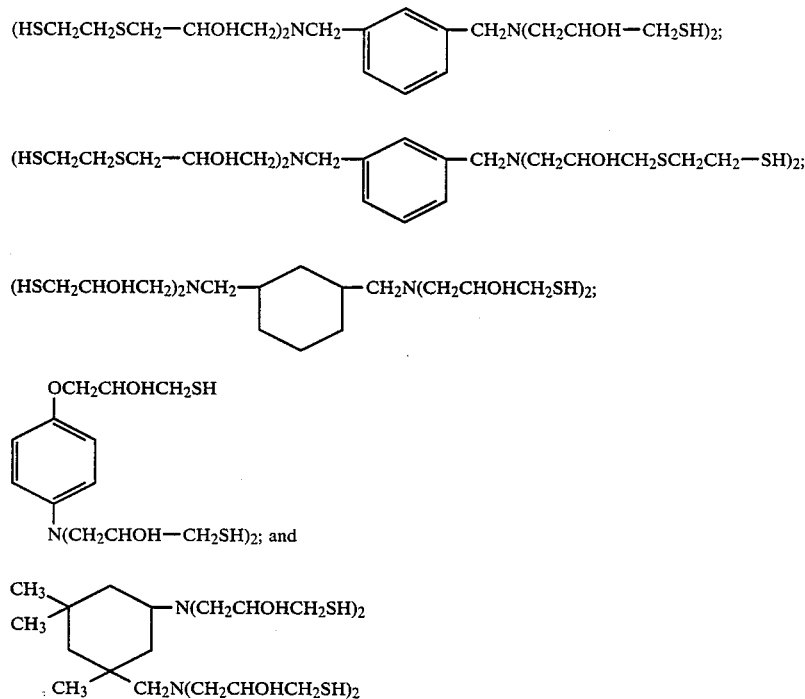

11. The product of claim 10 wherein said polythiol is:

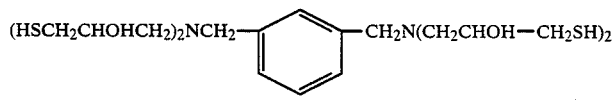

12. The product of claim 10 wherein said polythiol is:

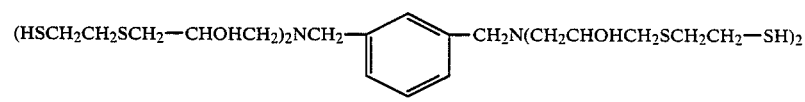

13. The product of claim 10 wherein said polythiol is:

14. The product of claim 10 wherein said polythiol is:

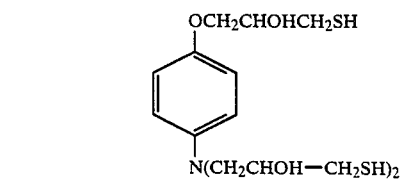

15. The product of claim 10 wherein said polythiol is:

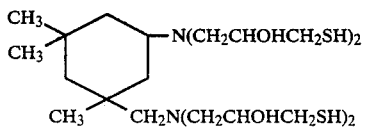

16. A process for curing polyepoxide comprising mixing together and reacting together
(a) at least one polyepoxide and
(b) at least one polythiol having the structure:

(XSCH$_2$CHOHCH$_2$)$_b$-A-R-N (CH$_2$CHOHCH$_2$SX)$_2$ wherein:
R is aromatic, substituted aromatic, methylene bis-diphenyl, xylylene, cycloaliphatic, substituted cycloaliphatic, methylene bis-dicyclohexyl, dimethylene cyclohexyl, methylene cyclohexyl or aliphatic,
A is N or O
X is -H or -R'SH,
R' is alkylene, cycloalkylene or alkylene substituted aromatic, and
when A is 0, b is 1 and when A is N, b is 2.

17. A process for curing polyepoxide comprising mixing together and reacting together
(a) at least one polyepoxide and
(b) at least one polythiol selected from the group consisting of:

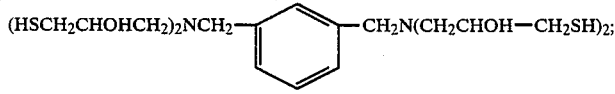;

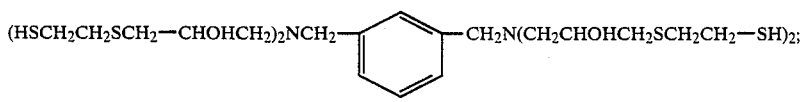;

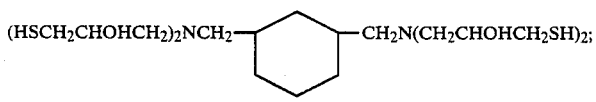;

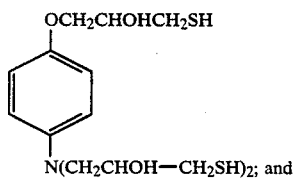; and

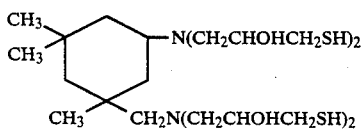

18. The process of claim 17 wherein said polythiol is:

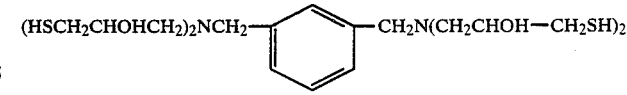

19. The process of claim 17 wherein said polythiol is:

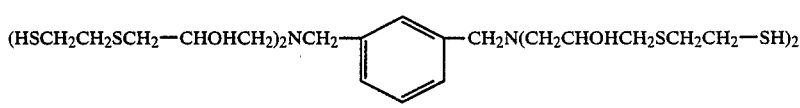

20. The process of claim 17 wherein said polythiol is:

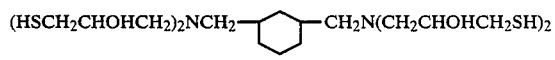

21. The process of claim 17 wherein said polythiol is:

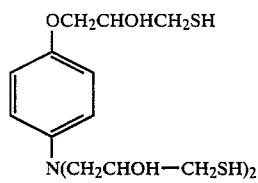

22. The process of claim 17 wherein said polythiol is:

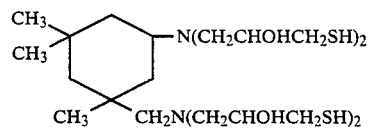

23. The process of claim 17 where there is present tertiary amine catalyst.

* * * * *